United States Patent
Ishibashi

(10) Patent No.: US 7,355,701 B2
(45) Date of Patent: Apr. 8, 2008

(54) SPECTROSCOPY ANALYSIS APPARATUS

(75) Inventor: Kiyochika Ishibashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 294 days.

(21) Appl. No.: 11/290,264

(22) Filed: Nov. 30, 2005

(65) Prior Publication Data
US 2006/0109461 A1    May 25, 2006

Related U.S. Application Data

(63) Continuation of application No. PCT/JP2004/007553, filed on May 26, 2004.

(30) Foreign Application Priority Data
May 30, 2003   (JP)   ............... 2003-155635

(51) Int. Cl.
G01J 3/00       (2006.01)
G01N 21/64      (2006.01)
(52) U.S. Cl. ............ 356/300; 356/326; 356/318; 250/458.1
(58) Field of Classification Search ........ 356/326, 356/318; 250/458.1; 700/59, 61, 64; 359/393
See application file for complete search history.

(56) References Cited
U.S. PATENT DOCUMENTS
6,320,196 B1   11/2001  Dorsel et al. ........... 250/458.1

FOREIGN PATENT DOCUMENTS
| JP | 9-113448 | 5/1997 |
| JP | 2001-194305 | 7/2001 |
| JP | 2002-139436 | 5/2002 |
| JP | 2004-108892 | 4/2004 |

OTHER PUBLICATIONS

Kinjo, M., "Protein nuclear acid enzyme", (1999), vol. 44N09, pp. 1431-1438.
Schwille, P. et al., "Dual-Color Fluorescence Cross-Correlation Spectroscopy for Multicomponent Diffusional Analysis in Solution", Biophysical Journal (1997), vol. 72, pp. 1878-1886.
Brinkmeier, M. et al., "Two-Beam Cross-Correlation: A Method To Characterize Transport Phenomena in Micrometer-Sized Structures", Analytical Chemistry (1999), vol. 71, No. 3, pp. 609-616.

*Primary Examiner*—F. L. Evans
*Assistant Examiner*—Abdullahi Nur
(74) *Attorney, Agent, or Firm*—Scully, Scott, Murphy & Presser, P.C.

(57) ABSTRACT

A spectroscopy analysis apparatus contains a focusing unit which focuses light from a light source on a sample, an optical scanner which scans the light on the sample, an optical detector which detects light intensity of the light emitted from the sample, and a cross-correlation calculating unit which calculates cross-correlation between the measurement points by associating light intensity with scanning position of the optical scanner, light intensity, which is detected with the optical detector, from plural measurement points on the sample, whose position is controlled with the optical scanner.

9 Claims, 10 Drawing Sheets

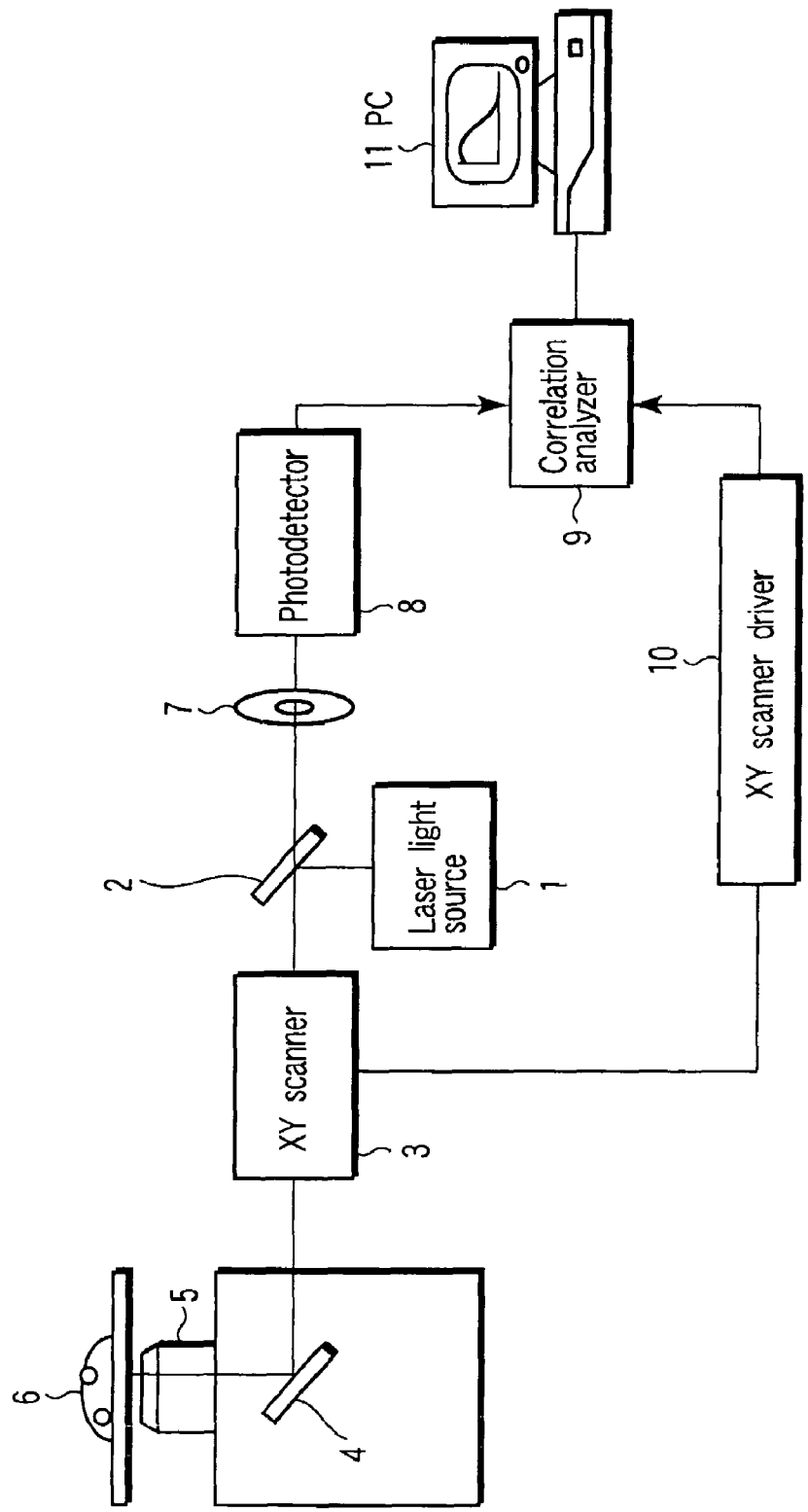
F I G. 3

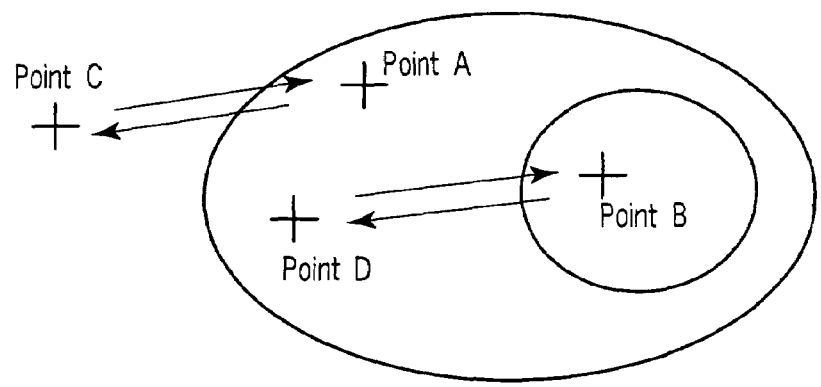
F I G. 10
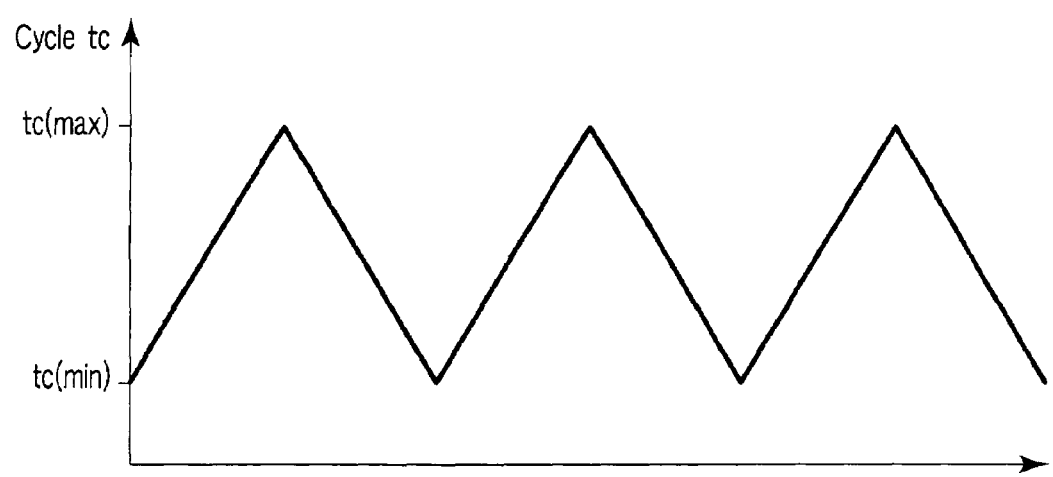
F I G. 11

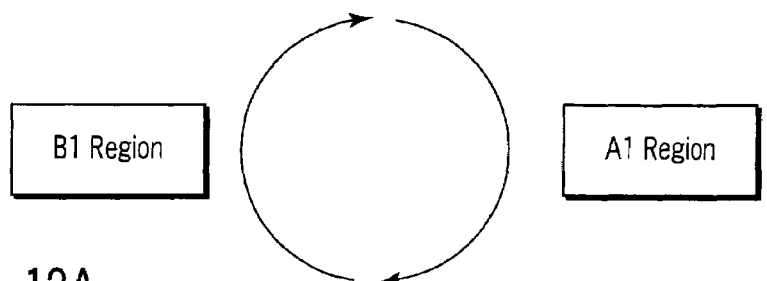
F I G. 12A
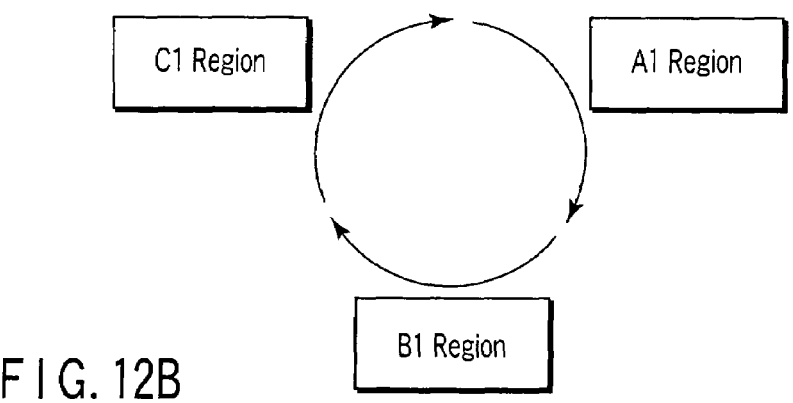
F I G. 12B
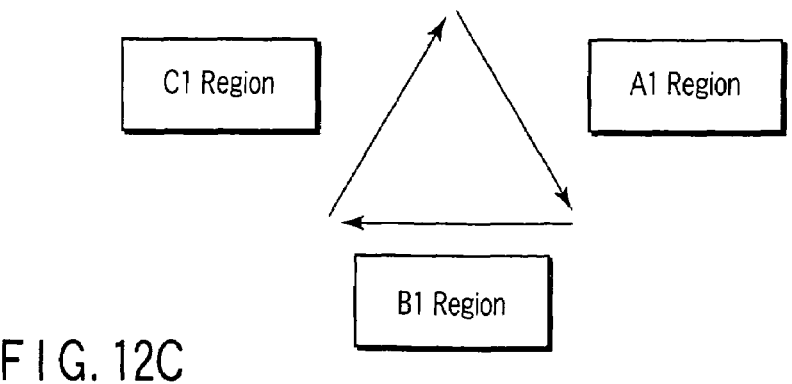
F I G. 12C

SPECTROSCOPY ANALYSIS APPARATUS

CROSS-REFERENCE TO RELATED APPLICATIONS

This is a Continuation Application of PCT Application No. PCT/JP2004/007553, filed May 26, 2004, which was published under PCT Article 21(2) in Japanese.

This application is based upon and claims the benefit of priority from prior Japanese Patent Application No. 2003-155635, filed May 30, 2003, the entire contents of which are incorporated herein by reference.

BACKGROUND OF THE INVENTION

1. Field of the Invention

The present invention relates to a spectroscopy analysis apparatus using a fluorescence correlation spectroscopy analysis technique for analyzing a state of fluorescence molecules by analyzing fluctuation of the fluorescence molecules in a biological sample. In particular, the present invention relates to a spectroscopy analysis apparatus for analyzing a correlation of fluorescence intensity between different measuring points.

2. Description of the Related Art

A fluorescence correlation spectroscopy analysis technique (FCS technique) is a technique of analyzing fluctuation of light produced by a Brown motion of fluorescence molecules in a microscopic monitoring region in a field of view of a microscope to obtain an auto-correlation function of fluorescence intensity and analyzing a dispersion time or an average number of molecules on a molecule by molecule basis. This technique is described in detail in "single molecule detection using a fluorescence correlation spectroscopy technique", Authored by KINJO, "Protein nuclear acid enzyme", 1999, vol. 44NO9 1431-1438, for example. When the fluorescence intensity is defined as I(t), the auto-correlation function can be expressed in the form of formula (1).

$$g(\tau) = \frac{\frac{1}{T}\int_0^T I(t)I(t+\tau)dt}{\left[\frac{1}{T}\int_0^T I(t)dt\right]^2} \quad (1)$$

FIG. 1 is a diagram showing an example of an optical system for used in measurement by such an FCS technique. In FIG. 1, a laser light source 100 is used as an excitation light source. The laser beam from the laser light source 100 is reflected on a dichroic mirror 101, and then is incident to an objective lens 102. A sample 103 labeled with a fluorescence dye is placed at a focal point of the objective lens 102. The laser beam focused at the focal portion by the objective lens 102 excites the fluorescence dye and induces fluorescence. The fluorescence emitted from the fluorescence dye of the sample 103 is captured again by the objective lens 102, and then reaches the dichroic mirror 101. The dichroic mirror 101 has optical characteristics that reflect excited light and transmits fluorescence. Thus, the fluorescence from the sample 103 passes through the dichroic mirror 101, and is focused by a focusing lens 104. A pin hole 105 is disposed at the focal point of the focusing lens 104. The fluorescence from a position other than the focal point of the objective lens 102 is interrupted by the pin hole 105, whereby high spatial resolution can be obtained. The fluorescence having passed through the pin hole 105 is incident to a photodetector 106, and the fluctuation of the fluorescence intensity is measured.

FIG. 2 is a diagram showing an example of an optical system such that the fluctuations of the fluorescence intensities at two measurement points can be measured at the same time. In FIG. 2, a laser light source 200 is used as an excitation light source. The laser beam which is the excited light from the laser light source 200 is split into two luminous fluxes by a beam splitter 201. The laser beams split into two luminous fluxes are reflected on mirrors 202 and 203, respectively, and combined again by a beam splitter 204. The two laser beams combined by the beam splitter 204 are reflected on the mirrors 202 and 203 such that their light axes are slightly shifted from each other. The combined light fluxes enter an objective lens 206 after they have been reflected on the dichroic mirror 205, and connects their focal points at two points which are slightly spaced from each other on a sample 207. Then, the fluorescence emitted from a focal region of each of the two points on the sample 207 is captured again by the objective lens 206. The captured fluorescence passes through the dichroic mirror 205 and is focused by a focusing lens 208 to connect their focal points at two points which correspond to the focal regions of the respective two points. Then, from this focal point, the resulting lights are incident to photodetectors 210a and 210b through optical fibers 209a and 209b, respectively, and the fluctuation of the fluorescence intensity of each light is measured. In this example, although no pin hole is used, core diameters of the optical fibers 209a and 209b function as pin holes.

A fluorescence cross-correlation spectroscopy analysis technique (FCCS technique) is devised as an analysis technique having enhanced the above-described fluorescence correlation spectroscopy analysis technique (FCS technique). The fluorescence cross-correlation spectroscopy analysis technique (FCCS technique) is a technique of obtaining a cross-correlation function between different fluorescence signals to analyze a correlation therebetween. In the fluorescence cross-correlation spectroscopy analysis technique (FCCS technique), there is a case in which a correlation is obtained with respect to two fluorescence dyes in an identical measurement point or a case in which a correlation is obtained between two measurement points. These cross-correlation functions are expressed in the form of formula (2). In formula (2), $I_{A(t)}$ and $I_{B(t)}$ designates their respective fluorescence intensity signals.

$$g(\tau) = \frac{\frac{1}{T}\int_0^T I_A(t)I_B(t+\tau)dt}{\frac{1}{T}\int_0^T I_A(t)dt \cdot \frac{1}{T}\int_0^T I_B(t)dt} \quad (2)$$

In the identical measurement point, cross-correlation analysis between dual-color fluorescence dyes is described in detail in "Dual-Color Fluorescence Cross-Correlation Spectroscopy for Multicomponent Diffusional Analysis in Solution, P. Schwille et al, Biophysical Journal 1997, 72, 1878-1886. This analysis is used for analysis of interaction between the molecules labeled with dual-color fluorescence dyes. A method of analyzing a correlation between different points is described in "Two-Beam Cross-Correlation: A method To Characterize Transport Phenomena in Micrometer Sized Structures", M. Brinkmeier et al, Anal. Chem.

1999, 71, 609-616, and a method of measuring a velocity and a direction of a flow of a fluid is introduced.

The fluorescence correlation spectroscopy analysis technique (FCS technique) and the fluorescence cross-correlation spectroscopy analysis technique (FCCS technique) are noticeable in advantage that measurement can be invasively carried out. In recent years, these techniques have been used for a non-homogenous sample such as a cell system. While avoiding the vicinity of a critical surface of a container in which a specific phenomenon such as adsorption is likely to occur, all locations are basically uniform in a solution system, and thus, it is possible to grasp an outlook of an entire system by measuring one point in solution. However, because different events occur at individual locations in a non-homogenous system such as a cell system, a measurement result greatly depends on a measurement location. In addition, in a non-homogenous system, in particular, in a cell system, the events between different points are associated with each other. There are many cases in which a certain event at a certain point has a temporal and spatial association such that it causes another event at another point. If an attempt is made to properly comprehend such a system, it is indispensable to carry out measurements between the different points at the same time. In recent years, there has been a growing demand for such a measurement among researchers.

As an optical system for carrying out fluorescence measurement among a plurality of measurement points at the same time, there has been proposed a method using a plurality of excitation light sources and a plurality of detectors, as disclosed in U.S. Pat. No. 6,320,196.

As another method, there has been proposed a method using an optical system which splits light excited from one excitation light source by a beam splitter and supplies the split light beams excited from such one excitation light source to a plurality of measurement points, as disclosed in Jpn. Pat. Appln. KOKAI Publication No. 9-113448.

In the method disclosed in U.S. Pat. No. 6,320,196, however, equipment becomes complicated because a plurality of optical systems each having an excitation light source and a detector are disposed. Further, a distance between measurement points is limited by a gap between the detectors, so that it is difficult to measure very close measurement points while individually tracking them.

In the method disclosed in Jpn. Pat. Appln. KOKAI Publication No. 9-113448, detectors are used independently on a measurement point by point basis, and thus, a complicated detecting optical system is unavoidable.

An optical system for use in fluorescence correlation spectroscopy analysis is used in combination of a laser and a photodetector with ultra-high sensitivity enabling single photon measurement. In general, these optical parts are very expensive. For this reason, installing these measuring systems in plurality makes equipment very expensive and large-sized. Moreover, in the case where a plurality of measurement points are set in a single cell, a gap between the measurement points becomes very small, is not always constant, and depends on cells targeted for measurement. In the conventional methods, it has been difficult to cope with these requests.

BRIEF SUMMARY OF THE INVENTION

It is an object of the present invention to provide a spectroscopy analysis apparatus which constantly enables measurement with high precision even if a gap between measurement points is very small. It is another object of the present invention to provide a small-sized, inexpensive spectroscopy analysis apparatus which enables cross-correlation analysis among a plurality of measurement points by an optical system provided in common.

A spectroscopy analysis apparatus is characterized by comprising: a focusing unit which focuses light from a light source on a sample; an optical scanner which scans the light on the sample; an optical detector which detects light intensity of the light emitted from the sample; and a cross-correlation calculating unit which calculates cross-correlation between the measurement points by associating light intensity with scanning position of the optical scanner, light intensity, which is detected with the optical detector, from plural measurement points on the sample, whose position is controlled with the optical scanner. The invention can be realized by method and/or computer program to achieve the feature of the spectroscopy analysis apparatus besides the spectroscopy analysis apparatus.

BRIEF DESCRIPTION OF THE SEVERAL VIEWS OF THE DRAWING

FIG. 3 is a diagram showing a schematic configuration of one embodiment of the present invention.

FIG. 10 is a schematic diagram planarly depicting how scanning is carried out in accordance with the modified example 1.

FIG. 11 is a view showing an example in the case where a measurement cycle of the modified example 1 has been varied.

FIGS. 12A to 12C are diagrams each showing an example in the case where XY scanner scanning according to a modified example 2 of the first embodiment is carried out in a closed loop shape.

DETAILED DESCRIPTION OF THE INVENTION

Figure 1:
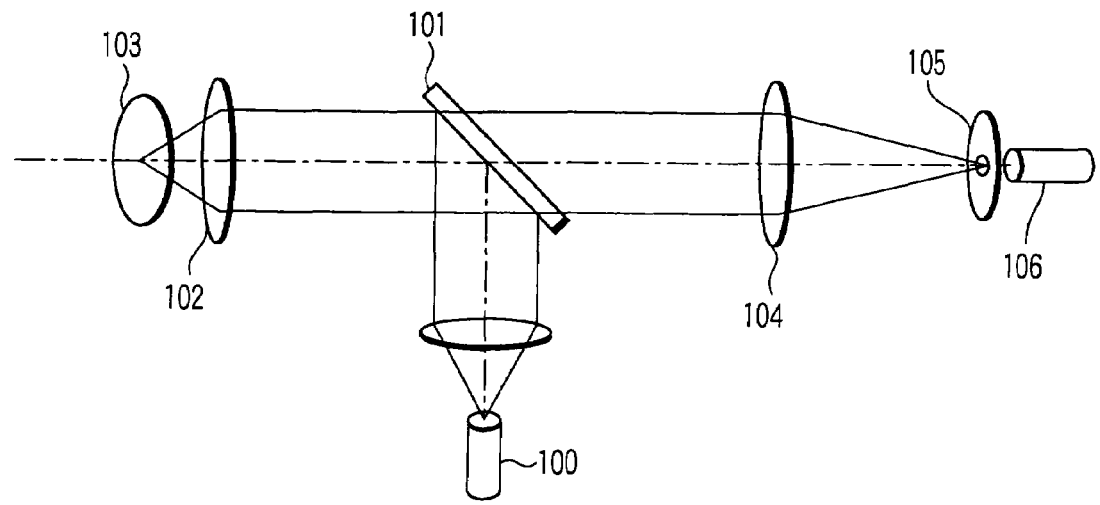
FIG. 1 is a diagram showing a schematic configuration of an example of a conventional optical system for use in measurement by an FCS technique.
Figure 2:
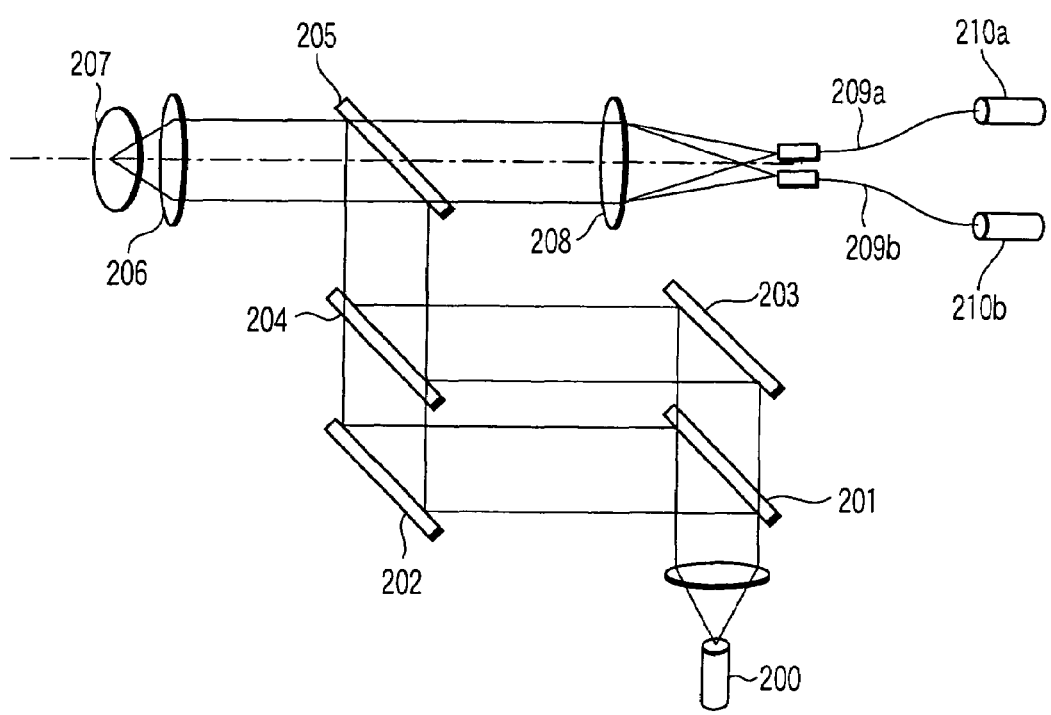
FIG. 2 is a diagram showing a schematic configuration of another example of the conventional optical system for use in measurement by the FCS technique.

Hereinafter, one embodiment of the present invention will be described with reference to the accompanying drawings.

FIG. 3 is a diagram showing a schematic configuration of one embodiment of a spectroscopy analysis apparatus to which the invention is applied. In FIG. 3, a dichroic mirror 2 is disposed in an optical path of laser beam from a laser light source 1 serving as an excitation light source. The dichroic mirror 2 has optical characteristics of reflecting excited light and transmitting fluorescence having a wavelength which is longer than that of the excited light.

An XY scanner 3 serving as an optical scanner is disposed in a reflection optical path of the dichroic mirror 2. The XY scanner 3 has two galvano mirrors (not shown) for deflecting light in two orthogonal directions. The laser beams reflected on the dichroic mirror 2 are deflected in a two-dimensional direction by the two galvano mirrors. Namely, by means of the XY scanner 3, incident lights can be deflected in an X axis and a Y axis, respectively, by an arbitrary angle. Here, the inside of the viewing field of an objective lens 5 described later can be raster-scanned, and arbitrary one or plural measurement points can be sequentially scanned or such scanning can be stopped.

The movements of the XY scanner 3 are controlled by an XY scanner driver 10.

The objective lens 5 is disposed via a mirror 4 in a reflection optical path of the XY scanner 3. A sample 6 labeled with a fluorescent pigment is disposed at a focal point of the objective lens 5.

A photodetector 8 serving as an optical detector is disposed via a pin hole 7 in a fluorescence transmission optical path of the dichroic mirror 2. The fluorescence of a position other than the focal point of the objective lens 5 is interrupted by means of the pin hole 7, and high spatial resolution can be obtained. The photodetector 8 detects intensity of the fluorescence having passed through the pin hole 7. An avalanche photo diode (APD), a photo multiplexer (PMT) or the like is used as the photodetector 8.

A correlation analyzer 9 serving as a cross-correlation calculating unit is connected to the photodetector 8. The XY scanner driver 10 is connected to the correlation analyzer 9. The correlation analyzer 9 calculates correlation while associating an intensity signal of the fluorescence from the photodetector 8 with positional information on a measurement point on the sample 6 from the XY scanner driver 10, and obtains a cross-correlation function between the measurement points.

A personal computer (PC) 11 is connected to the correlation analyzer 9. The PC 11 processes an analysis result at the correlation analyzer 9, and displays the result on a monitor.

In the above-described configuration, first, an operation of whole equipment will be briefly described here.

When laser beam serving as excited light is emitted from the laser light source 1, the laser beam is reflected on the dichroic mirror 2 and is incident to the XY scanner 3. The laser beam deflected by the XY scanner 3 is focused by the objective lens 5, and connect a focal point at a position on the sample 6 which corresponds to the XY deflection of the XY scanner 3.

The fluorescence dye is excited at the focal point in the sample 6, and fluorescence is emitted. The fluorescence emitted from the fluorescence dye is captured by the objective lens 5, and the captured fluorescence is guided to the dichroic mirror 2 though a reverse optical path. The guided fluorescence transmits the dichroic mirror 2, and is incident to the pin hole 7.

The pin hole 7 interrupts the fluorescence from a position other than the focal point of the objective lens 5, and only the fluorescence having passed through the pin hole 7 is incident to the photodetector 8.

The intensity signal of the fluorescence which has been photoelectrically converted by the photodetector 8 is inputted to the correlation analyzer 9. The correlation analyzer 9 calculates correlation while associating the intensity signal of the fluorescence from the photodetector 8 with positional information on the measurement point on the sample 6 from the XY scanner driver 10, and obtains a cross-correlation function between the measurement points.

Hereinafter, a cross-correlation calculation at the correlation analyzer 9 will be described here. Here, a description will be given with respect to a case of repeatedly scanning two measurement points on the sample 6, and detecting the fluorescence intensities at the respective measurement points.

Figure 4:
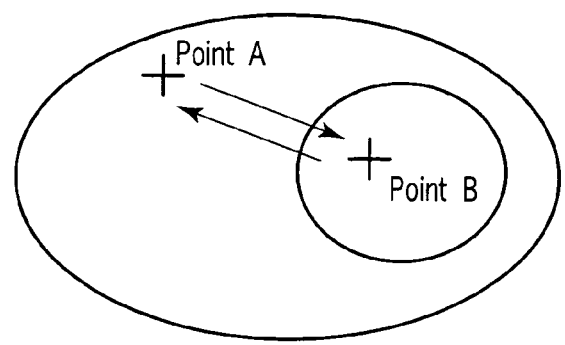
FIG. 4 is a schematic diagram planarly depicting how to scanning is carried out in accordance with a first embodiment.

In this case, the XY scanner 3, as shown in FIG. 4, stops at one measurement point A for a predetermined time ($t_w$), for example, 1 ms, and then, moves to a next measurement point B. At this measurement point B, the scanner stops for a predetermined time ($t_w$), for example, 1 ms. The XY scanner 3 then reverts to the measurement point A. The XY scanner 3 repeatedly executes operation, and scans a sample.

Figure 5:
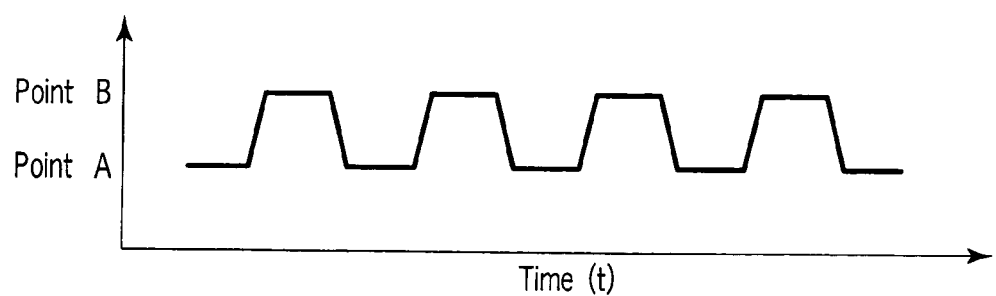
FIG. 5 is a view schematically depicting a relationship between a time and a scanning position in accordance with the first embodiment.
Figure 6:
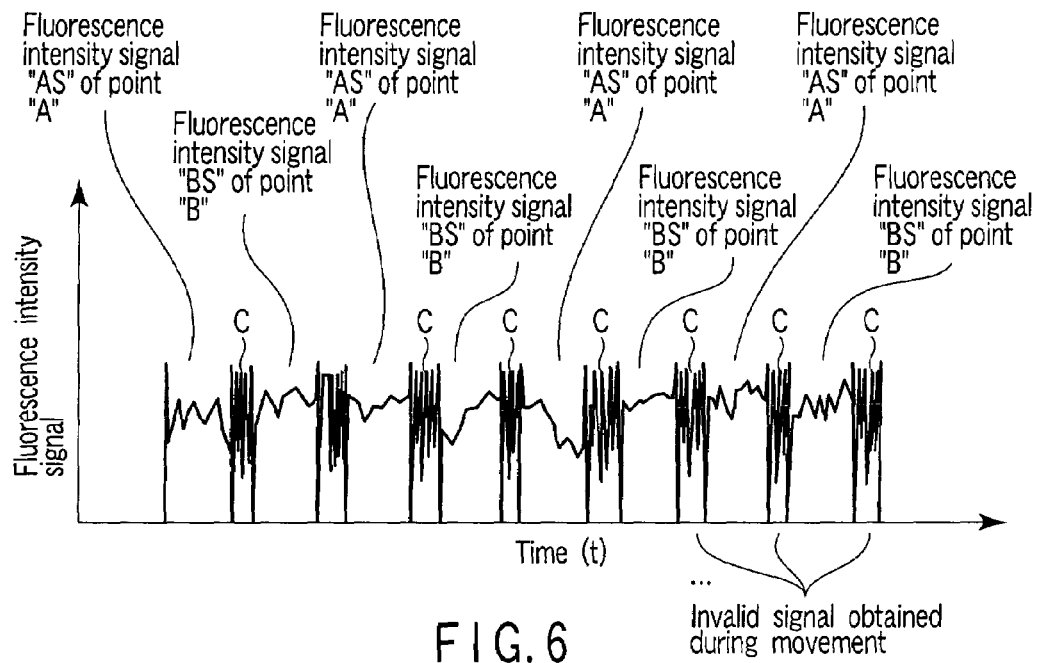
FIG. 6 is a view showing a state of a signal outputted from a photodetector in accordance with the first embodiment.

FIG. 5 is a view schematically depicting a relationship between a time and a scanning point. As shown in FIG. 5, a scanning position by the XY scanner 3 moves alternately between the measurement points A and B with an elapse of time "t", and stops at the measurement points A and B, respectively, for a predetermined time. Then, during the scanning by the XY scanner 3, the fluorescence intensities at the respective measurement points A and B (including movement in progress) are measured. Consequently, a signal outputted from the photodetector 8, as shown in FIG. 6, is produced as a signal mixed with an invalid signal C during movement from the measurement point A to the measurement point B in addition to a fluorescence intensity signal AS measured at the measurement point A and a fluorescence intensity signal BS measured at the measurement point B.

In addition to the fluorescence intensity signal AS at the measurement point A and the fluorescence intensity signal BS at the measurement point B, the signal mixed with the invalid signal C is given as an input signal to the correlation analyzer 9. Then, the correlation analyzer 9 obtains a cross-correlation function between two points by calculates correlation such that the fluorescence intensity signals AS and BS are associated with positional information on the measurement points A and B (positional information on the measurement points A and B of the XY scanner 3 by the XY scanner driver 10). Now, a method of obtaining a cross-correlation function between two points will be described here.

Figure 7:
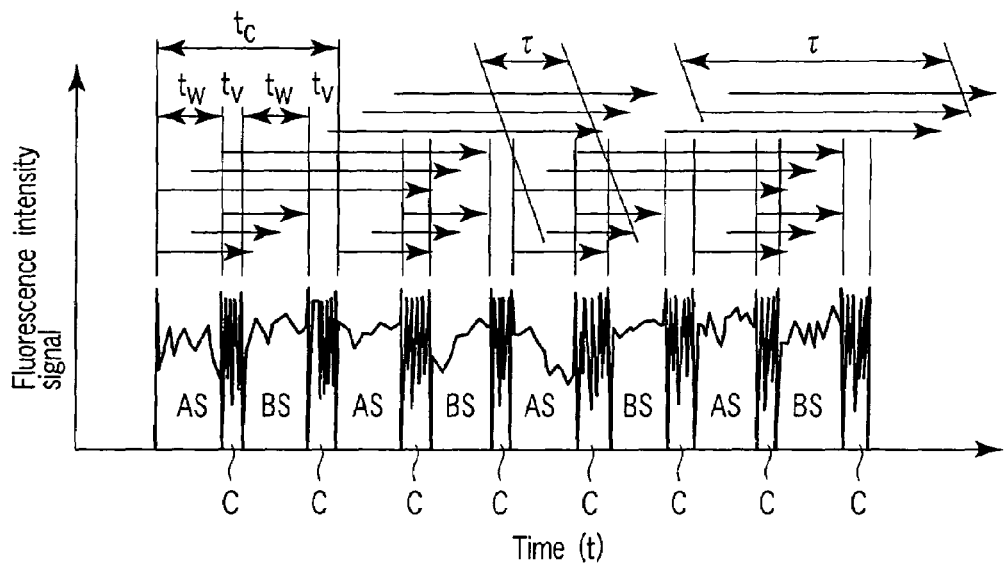
FIG. 7 is a view illustrating a first method of obtaining a cross-correlation function between two points in accordance with the first embodiment.

A first method will be described with reference to FIG. 7.

Let us consider a time τ which has been elapsed until the fluorescence intensity signal BS at the measurement point B exists from a time point of detecting the fluorescence intensity signal AS at the measurement point A. In the first method, with respect to a range of the time τ, a cross-correlation function between two points is obtained by partially integrating and calculating the detection signal. In this case, measurement times at the measurement points A and B are designated by $t_w$; an invalid time having the invalid signal C moving from the measurement point A to the measurement point B is designated by $t_v$; and a measurement cycle is designated by $t_c$. A minimum value of the time τ is a valid time $t_v$ from a time when the last data on the fluorescence intensity signal AS at the measurement point A has been obtained to a time when the first data on the fluorescence intensity signal BS at the measurement point B has been obtained. Then, a maximum value of the time τ within the measurement cycle $t_c$ is up to $2t_w+t_v$ from the time when the first data on the fluorescence intensity signal AS at the measurement point A has been obtained to the time when the last data on the fluorescence intensity signal BS at the measurement point B has been obtained. Therefore, the time τ is obtained as a continuous value which is $t_v$ or more and $2t_w+t_v$ or less (refer to formula (3)).

Further, the time τ which is greater than the measurement cycle $t_c$ does not exist until the fluorescence intensity signal BS at the measurement point B appears. Accordingly, the time τ is obtained by a discontinuous formula in which the measurement cycle is defined as $t_c$, and formula (3) can be expressed as a general formula as in formula (4).

$$t_v \leq \tau \leq 2t_w + t_v \quad (3)$$

$$jt_c + t_v \leq \tau \leq jt_c + 2t_w + t_v \quad (4)$$

Where, j: 0, 1, 2, 3, . . .

However, even if the time τ is within the range of formula (4), a combination, in which the fluorescence intensity signal BS at the measurement point B exists at a location at which a time has been elapsed by τ from the fluorescence intensity signal AS at the measurement point A, is partial of a whole. Therefore, a cross-correlation value with respect to the corresponding time τ can be obtained by partially integrating only the range of a combination which satisfies the combination in which the fluorescence intensity signal BS exists. An example of this partial integration is represented by formula (5). Formula (3) to formula (5) are examples of a case corresponding to FIG. 7, and the calculation of a partial integration does not always take the same aspect.

$$g(\tau) = \frac{(J+1)(2t_w + t_w - \tau') \sum_{j=0}^{J} \int_{0}^{2t_w+t_w-\tau'} I_A(Jt_c + t) I_B(Jt_c + t + kt_c + t + \tau') dt}{\sum_{j=0}^{J} \int_{0}^{2t_w+t_w-\tau'} I_A(Jt_c + t) dt \sum_{j=0}^{J} \int_{0}^{2t_w+t_w-\tau'} I_B(Jt_c + t) dt} \quad (5)$$

Where, j: 0, 1, 2, 3, . . .

$t_v \leq \tau \leq 2t_w + t_v$ $\tau = kt_c + \tau'$ k: 0, 1, 2, 3, . . .

In the case of a direction moving from the measurement B to the measurement point A, it is designated as a negative value of τ. Although the above method can be obtained only in the range such that the time τ is greater than the invalid time $t_v$, it can be eventually regarded as τ=0 if the invalid time $t_v$ is sufficiently small as compared with a measurement event.

Figure 8:
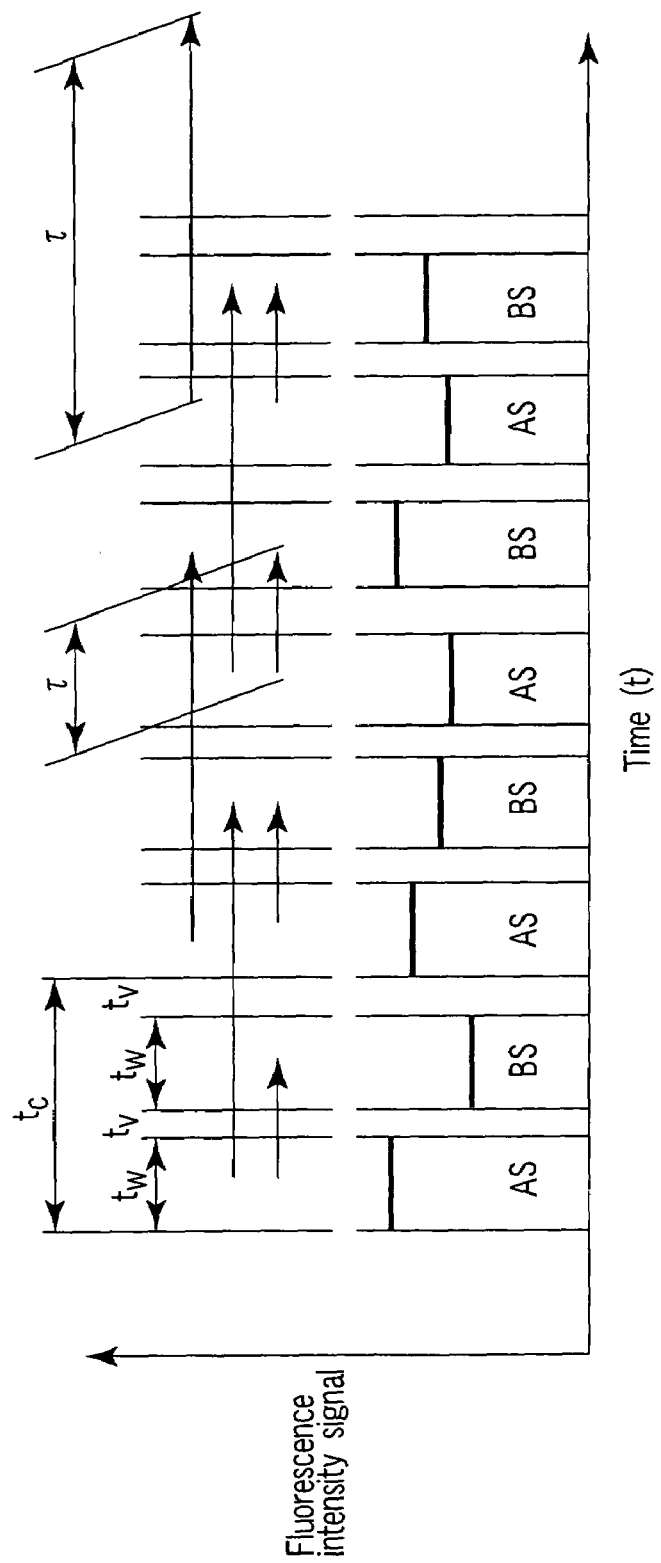
FIG. 8 is a view illustrating a second method of obtaining a cross-correlation function between two points in accordance with the first embodiment.

A second method will be described here. In the second method, the fluorescence intensity signals AS and BS (fluorescence intensity values) acquired within the time $t_w$, respectively, at the measurement points A and B are temporarily converted to single or plural statistical values so as to calculate a correlation function by using these statistical values. In this case, as the statistical values, an average value of the fluorescence intensity signals AS and BS at the measurement points A and B acquired within each time $t_w$ is used as shown in FIG. 8. In addition, a calculating example is represented by formula (6).

$$g(\tau) = \frac{J \sum_{j=0}^{J} S_A(j) S_B(j+k)}{\sum_{j=0}^{J} S_A(j) \sum_{j=0}^{J} S_B(j)} \quad (6)$$

Where, $\tau = kt_c + t_w/2$ k: 1, 3, 5, 7, . . .

A minimum value of the time τ at this time is obtained as $t_c$, and then, is discretely assigned by the integer multiple.

In the second method, although the minimum value of τ is greater as compared with the first method, it can be eventually regarded as τ=0 if $t_c$ is sufficiently small as compared with a measurement event. In addition, the second method is suitable to speed up calculation with a small number of integrating calculations. Further, in the second method, a gate as (not shown) is opened only during the time $t_w$ for acquiring the fluorescence intensity signals AS and BS, an output from the photodetector is counted, whereby the counted value may be directly used for correlation calculation. Thus, there is provided an advantage that equipment configuration can be simplified.

In the second method, an average value has been used as a statistical value without being limited thereto. For example, an integral value of fluorescence intensities or a sum of photo counts may be used. Further, it is possible to improve an S/N ratio by carrying out statistical processing such as employing an average weighted with respect to a time or selectively using only a value which exceeds a threshold value.

According to the above-described embodiment, while measurement points A and B are alternately moved by means of scanning of the XY scanner 3, the fluorescence intensity signals AS and BS at the respective measurement points A and B are measured by the photodetector 8 so as to calculates correlation between the measurement points A and B while the fluorescence signal signals AS and BS are associated with positional information at the measurement points A and B of the XY scanner 3. Therefore, an optical system provided in common can carry out cross-correlation analysis among a plurality of measurement points alone. In this manner, a simplified equipment configuration can be achieved, and equipment downsizing and inexpensive equipment can be achieved.

In addition, since measurement points on the sample 6 are set by the scanning by the XY scanner 3 in an XY direction, it is possible to dispose a plurality of measurement points in proximity to each other. Consequently, in particular, in measurement targeted for cells serving as the sample 6, a result can be speedily obtained while they are alive, and a scanning length is set to a length according to a desired distance between points. Therefore, there can be provided an optimal effect for analysis of biological molecules such as minimization of wasteful data or improvement of analysis precision.

While the foregoing embodiment has described a case in which two measurement points exist (and a case of one-dimension), the number of measurement points may be three or more or may be in a two dimensional manner or in a three-dimensional manner. If three or more measurement points exist, it is preferable to design a program so as to set all points in a passage such that these points can be passed at the shortest distance.

In addition, the foregoing embodiment has described that scanning of the XY scanner 3 is temporarily stopped at each measurement value point so as to measure the fluorescence intensity signal. However, the fluorescence intensity signal is measured while always moving (scanning) the XY scanner 3, whereby correlation may be calculated with respect to only a specific position.

Further, in the case where ringing is excessive when the XY scanner 3 stops, the scanner has stopped at a target position, and then, a fluorescence intensity signal may be measured after ringing has stopped.

MODIFIED EXAMPLE 1

In the case where a time difference of τ generated by scanning becomes a problem because a speed of a measurement event is high, two XY scanners may be used.

Figure 9:
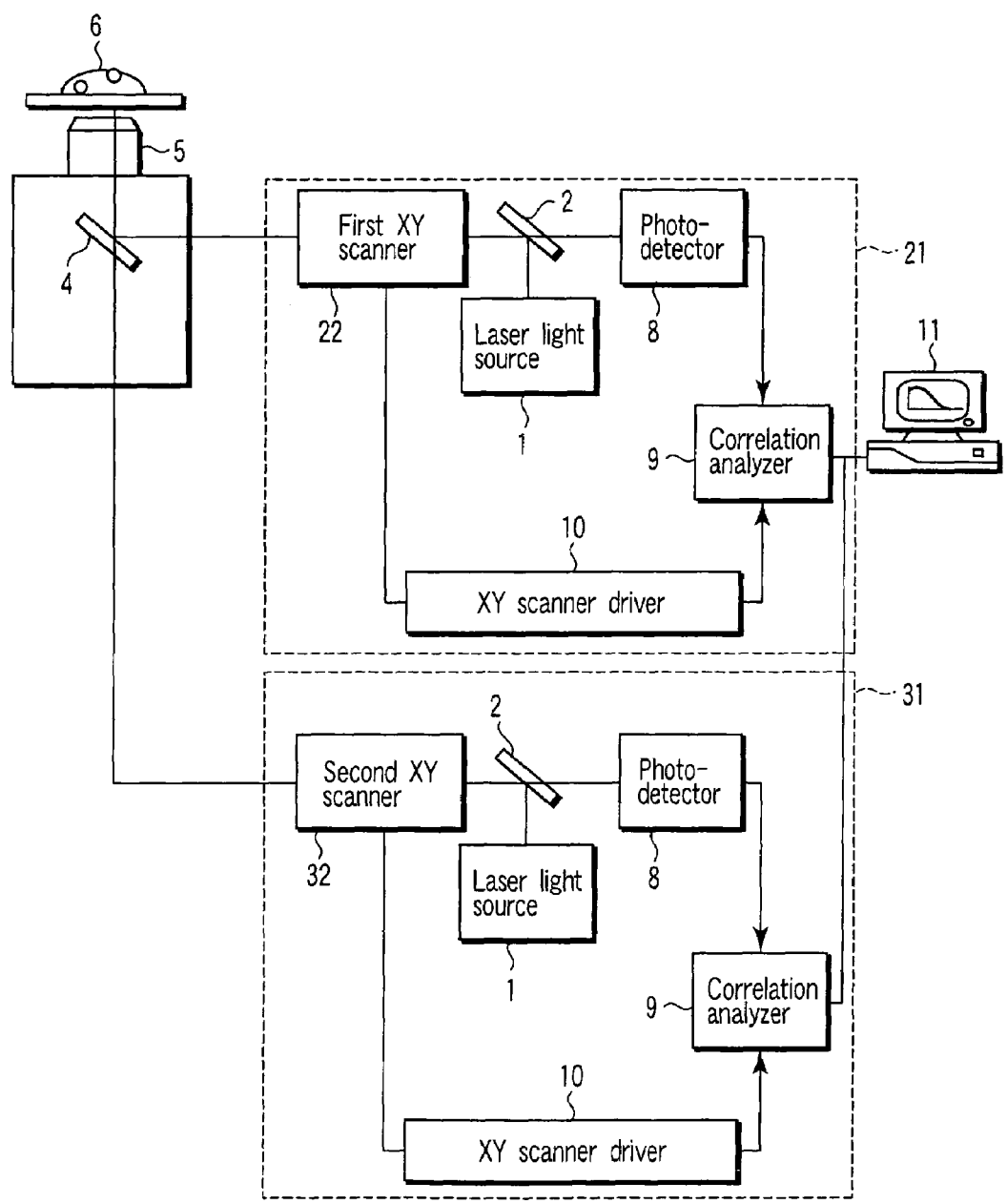
FIG. 9 is a diagram showing a schematic configuration of a modified example 1 of the first embodiment.

FIG. 9 is a diagram showing a schematic configuration of a modified example using two XY scanners. Like constituent elements in FIG. 3 are designated by like reference numerals.

In FIG. 9, the objective lens 5 and the sample 6 described in FIG. 3 are used in common, and two configurations of other portions are prepared. Scanning is carried out while a first XY scanner 22 of a first optical system 21 and a second XY scanner 32 of a second optical system 31 are synchronized with each other.

By doing this, although the optical systems become slightly complicated, a cross-correlation value of τ=0 can be obtained with high precision by carrying out scanning while the first XY scanner 22 and the second XY scanner 32 are synchronized with each other, for example, repeatedly scanning in a one-dimensional manner between the measurement points A and C by use of the first XY scanner 22 as shown in FIG. 10 and by repeatedly scanning in a one-dimensional manner between the measurement points B and D by use of the second XY scanner 32.

The measurement cycle $t_c$ and measurement time $t_w$ may be a variable value instead of a fixed value. FIG. 11 shows an example in the case where the measurement cycle $t_c$ has been varied from the maximum to the minimum with an elapse of time. By doing this, it becomes possible to reduce an interval at which a value of τ does not exist.

According to the modified example 1, a modification effective to scanning a luminous flux while optical precision is stabilized can be provided by using the objective lens 5 and the sample 6 in common.

MODIFIED EXAMPLE 2

Figure 13:
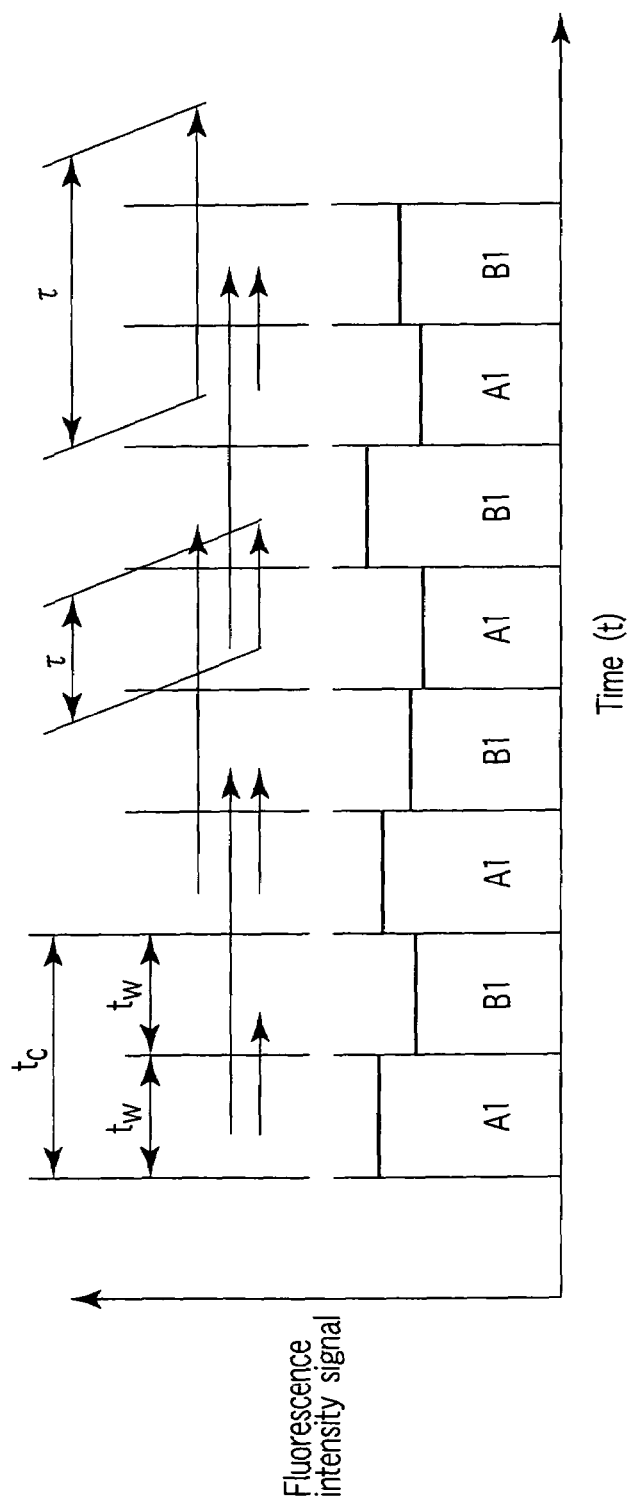
FIG. 13 is a view showing a state of a signal outputted from the photodetector in accordance with the modified example 2.

Scanning of the XY scanner 3 is repeatedly carried out in a closed loop shape, and one turn of this loop is divided into a plurality of regions, whereby correlation may be calculated between these divided regions. FIG. 12A shows a case where the shape of the scanning loop is circular, in which one turn of such a circular loop is divided into two equal regions A1 and B1 so as to calculates correlation between fluorescence intensity signals acquired in the regions A1 and B1. FIG. 13 is a view schematically depicting a relationship between a time and a position in this case. The fluorescence intensities at the respective measurement points in the regions A1 and B1 are measured while the regions A1 and B1 are passed alternately. In FIG. 13, $t_w$ denotes a measurement time at the region A1 or B1, and $t_c$ denotes a measurement cycle. Then, a method of obtaining a cross-correlation function between the regions A1 and B1 may be the first method, although it is preferable to use the second method.

FIG. 12B shows an example in which circular loop scanning has been divided into three equal regions A1, B1, and C1. FIG. 12C shows an example in which triangular loop scanning has been divided into three equal regions A1, B1, and C1. In this way, the shape of loop scanning may be circular or polygonal. In addition, a scanning pattern may be formed in a shape of a one stroke trajectory other than a loop, or may be two-dimensional scanning or three-dimensional scanning.

Of course, the number of divisions may be four or more. When each region is equally divided, a cross-correlation function between the regions becomes symmetrical if no environmental difference occurs. Further, the number of divisions, a distance between points, and a scanning shape or pattern may be variously combined with each other. Therefore, scanning between the points for correlation analysis can be random scanning. A change of a scanning pattern is executed in such a manner that the scanner driver 10 shown in FIG. 3 controls the XY scanner 3 to be driven through an automatic or manual input command in accordance with the number of measurement points which have been detected by the photodetector 8.

According to the modified example 2, symmetry of cross-correlation between the regions are compared and analyzed, whereby, for example, in the case where the sample 6 is a biological sample in a state in which a substance targeted for measurement such as a cell or a micro floe cell is included in a solution, it is possible to acquire information relating to convection or scattering inside of such cells or micro flow cells and other signal transmission direction or velocity.

MODIFIED EXAMPLE 3

Figure 14:
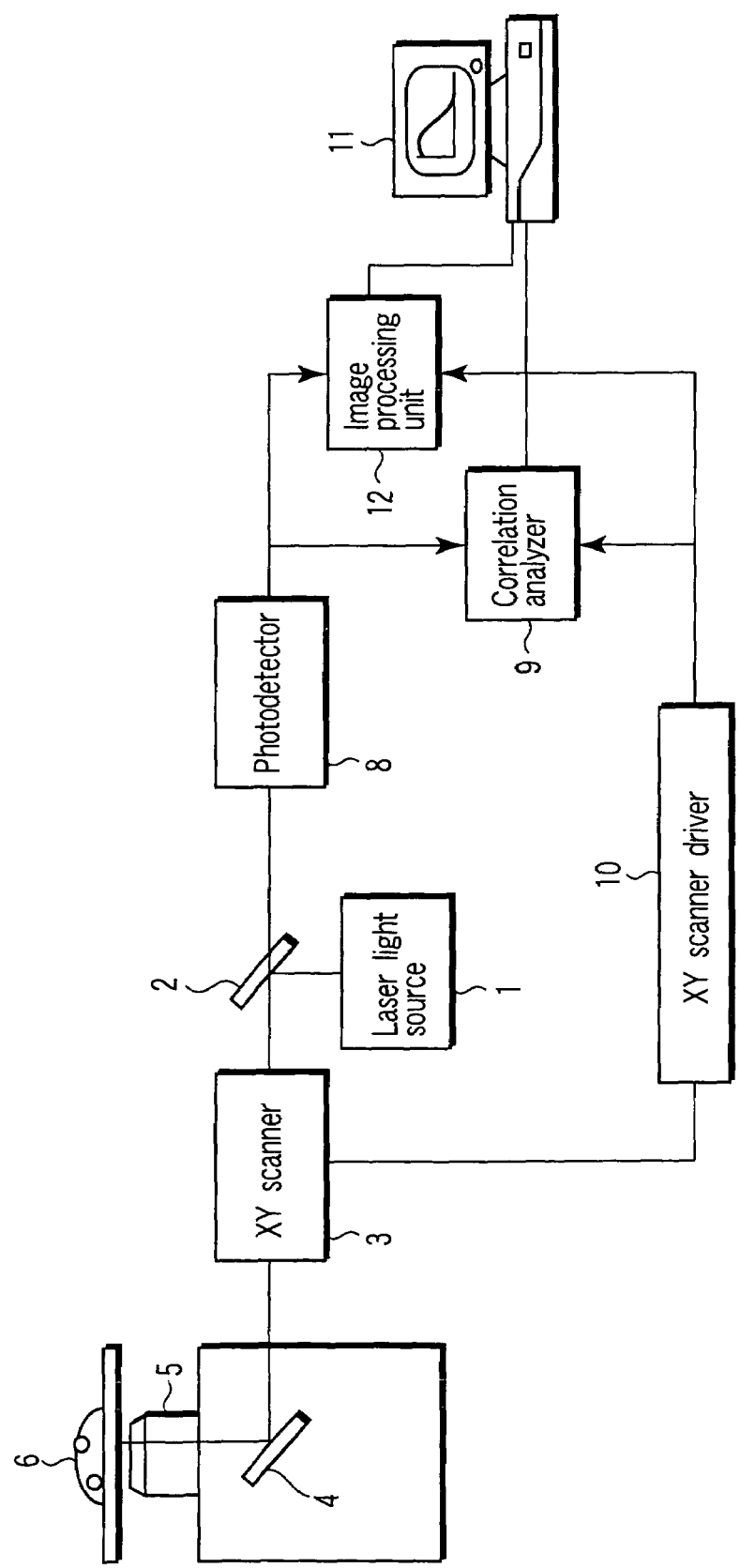
FIG. 14 is a diagram showing a schematic configuration of a modified example 3 of the first embodiment.

A system of measuring a fluorescence intensity signal can attain its advantageous effect greatly when the system is used in combination with a microscopic image acquisition system. In particular, because the optical systems are analogous to each other, more advantageous effect can be attained in accordance with a combination with a confocal laser scanning microscope. For example, the XY scanner driver 10 can provide a scan change type spectroscopy analysis apparatus such that regular and linear raster scanning and random non-raster scanning are switched from each other with respect to the XY scanner 3 having a scan mechanism capable of switching. By using such a new spectroscopy analysis apparatus, speedy scanning can be realized as compared with a case in which only raster scanning is executed in such a manner that at the time of image acquisition, servo system raster scanning is comprehensively executed, and that at the time of optical detection relevant to a plurality of measurement points during imaging, random scanning as described above is carried out. This fact leads to a result of high precision because a plenty of measurement values are effectively obtained from a plurality of measurement points in correlation analysis. In this case, an image processing unit 12 for image acquisition is provided in addition to a correlation analyzer 9 as shown in FIG. 14 in which like constituent elements in FIG. 3 are designated by like reference numerals, so that a fluorescence intensity signal from the photodetector 8 is inputted to the correlation analyzer 9 and image processing unit 12. Then, the results obtained by the correlation analyzer 9 and image processing unit 12 are outputted to the PC 11.

In this case, the photodetector 8 is used in common with respect to the correlation analyzer 9 and the image processing unit 12. However, an avalanche photo diode may be used for the correlation analyzer 9, and another photodetector such as a photoelectric multiplexer may be used for the image processing unit 12.

In addition, the invention is not limited to the foregoing embodiment, but various modifications can occur without departing from the spirit of the invention at a stage at which the invention is carried out. For example, while the foregoing embodiment has described that a galvano mirror is adopted as a scanning device, other means such as vibrating an optical fiber may be provided as long as a high speed scanning device is used. If possible, two-dimensional and three-dimensional scanning devices may be adopted with respect to an arbitrary combination of X, Y, and Z axes. In addition, single or multiple fluorescence dyes may be used. Further, the light intensity to be measured may be a correlation relevant to interaction among a plurality of points caused by an optical signal other than the above-described signals, for example, electrochemical light emission, fluorescence resonance energy transition and the like. Furthermore, as a result of the cross-correlation analysis, individual reaction results may be outputted with respect to two or more measurement points at which no correlation exists or at which correlation property is low. Moreover, the foregoing embodiment has described that a laser light source is used as a light source, but a xenon lamp, a mercury lamp or the like may be used as a light source.

Further, the foregoing embodiment includes inventions at a variety of stages, a variety of inventions can be extracted in accordance with a proper combination of a plurality of constituent elements disclosed herein. For example, even if some of all the constituent elements disclosed in the embodiment are erased, a problems described in the Problem to be Solved by the Invention section can be solved. In the case where the advantageous effect described in the Advantages of the Invention section can be attained, a configuration from which these constituent elements have been erased can be extracted as an invention.

According to the embodiment of the invention, even if a plurality of measurement points are very close to each other, cross-correlation analysis with high precision can be stably carried out. In addition, since fluorescence intensity information on a plurality of measurement points can be measured by an optical scanner of an optical system provided in common, it is possible to achieve cross-correlation analysis between these measurement points with a simple configuration.

Also, according to the embodiment of the invention, it becomes possible to dispose a plurality of measurements in proximal to each other by using the optical scanner, and optimal advantageous effect can be attained for measurement of cells.

In addition, according to the embodiment of the invention, cross analysis can be carried out while linking with image acquisition by applying a novel spectroscopy analysis device capable of switching different scanning patterns.

Further, according to the embodiment of the invention, scanning of the optical scanner is repeatedly carried out in a loop manner, and a cross-correlation function among a plurality of regions is obtained, thereby making it possible to carry out comparison, analysis and the like of symmetry of cross-correlation between the regions.

Therefore, according to the embodiment of the invention, there can be provided a small sized, inexpensive spectroscopy analysis apparatus capable of carrying out cross-correlation analysis among a plurality of measurement points by means of an optical system provided in common.

While the foregoing embodiment has described that the invention is an apparatus invention, the apparatus invention is also compatible with a method or program invention for achieving an operation of the above apparatus without being limited thereto.

What is claimed is:

1. A spectroscopy analysis apparatus comprising:
   a focusing unit which focuses light from a light source on a sample;
   an optical scanner which scans the light on the sample;
   an optical detector which detects light intensity of the light emitted from the sample; and
   a cross-correlation calculating unit which calculates cross-correlation between the measurement points by associating light intensity with scanning position of the optical scanner, light intensity, which is detected with the optical detector, from plural measurement points on the sample, whose position is controlled with the optical scanner.

2. A spectroscopy analysis apparatus according to claim 1, wherein
   the optical scanner repeatedly scans said at least two measurement points, and
   the cross-correlation calculating unit calculates cross-correlation between the measurement points by associating accumulation of light intensity of the optical detector at said at least two measurement points with scanning position of the optical scanner.

3. A spectroscopy analysis apparatus according to claim 1, wherein
   the optical scanner carries out repetitive scanning in a closed looped-shape, and
   the cross-correlation calculating unit divides one turn of the loop into a plurality of regions, and calculates cross-correlation between two regions by associating accumulation of light intensity of the optical detector at the measurement points in at least two regions of the divided regions with scanning position of the optical scanner.

4. A spectroscopy analysis apparatus according to claim 1, wherein the cross-correlation calculating unit temporarily converts light intensity of the optical detector at the measurement points to single or plural statistical values, and calculates cross-correlation by using these statistical values.

5. A spectroscopy analysis apparatus according to claim 1, wherein the optical scanner changes a scanning pattern in accordance with the number of the measurement points.

6. A spectroscopy analysis apparatus according to claim 1, wherein the optical scanner includes a function of a scanning system for image acquisition of the sample.

7. A spectroscopy analysis apparatus according to claim 6, wherein the optical scanner switches optical scanning for optical detection and optical scanning for image acquisition to different scanning patterns.

8. A spectroscopy analysis apparatus according to claim 1, wherein the optical scanner has a plurality of scanning optical systems.

9. A program for executing spectroscopy analysis, comprising:
   optical scanning means for scanning, on a sample, light from a light source, the light being focused on the sample; and
   cross-correlation calculating means for calculating cross-correlation between the measurement points by associating light intensity with scanning position of the optical scanner, light intensity, which is detected with the optical detector, from plural measurement points on the sample, whose position is controlled with the optical scanner.

* * * * *